(12) United States Patent
Condeelis et al.

(10) Patent No.: US 12,174,190 B2
(45) Date of Patent: Dec. 24, 2024

(54) COMBINED MARKERS FOR METASTATIC CANCER AND USES THEREOF

(71) Applicant: Albert Einstein College of Medicine, Bronx, NY (US)

(72) Inventors: John S. Condeelis, Bronx, NY (US); Maja H. Oktay, Rye, NY (US); Joan Jones, Bronx, NY (US); David Entenberg, Granite Springs, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 1093 days.

(21) Appl. No.: 16/955,289

(22) PCT Filed: Dec. 18, 2018

(86) PCT No.: PCT/US2018/066148
§ 371 (c)(1),
(2) Date: Jun. 18, 2020

(87) PCT Pub. No.: WO2019/126112
PCT Pub. Date: Jun. 27, 2019

(65) Prior Publication Data
US 2020/0393467 A1 Dec. 17, 2020

Related U.S. Application Data

(60) Provisional application No. 62/607,438, filed on Dec. 19, 2017.

(51) Int. Cl.
*G01N 33/574* (2006.01)
*G06T 7/00* (2017.01)
*G16H 30/00* (2018.01)

(52) U.S. Cl.
CPC ..... *G01N 33/57426* (2013.01); *G06T 7/0012* (2013.01); *G01N 2800/52* (2013.01); *G06T 2207/10056* (2013.01); *G16H 30/00* (2018.01)

(58) Field of Classification Search
None
See application file for complete search history.

(56) References Cited

U.S. PATENT DOCUMENTS

| | | |
|---|---|---|
| 2010/0047240 A1 | 2/2010 | Condeelis et al. |
| 2011/0059470 A1 | 3/2011 | Condeelis et al. |
| 2013/0156279 A1 | 6/2013 | Schoenmeyer et al. |

OTHER PUBLICATIONS

Harney, Allison S., et al. "Real-time imaging reveals local, transient vascular permeability, and tumor cell intravasation stimulated by TIE2hi macrophage-derived VEGFA." Cancer discovery 5.9 (2015): 932-943.*

Pignatelli et al., "Invasive breast carcinoma cells from patients exhibit MenaINV- and macrophage-dependent transendothelial migration", Sci Signal., Nov. 2014, vol. 7, No. 353, pp. 1-12.

Agarwal et al., "Quantitative assessment of invasive mena isoforms (Menacalc) as an independent prognostic marker in breast cancer", Breast Cancer Res., Sep. 2012, vol. 14, No. 5, pp. 1-8.

* cited by examiner

*Primary Examiner* — G. Steven Vanni
(74) *Attorney, Agent, or Firm* — Fox Rothschild LLP

(57) ABSTRACT

A combination of markers (TMEM, MenaCalc, and MenaINV) for hematogenous metastatic cancer and their use for diagnosis, prognosis and predictive performance are disclosed.

25 Claims, 12 Drawing Sheets
Specification includes a Sequence Listing.

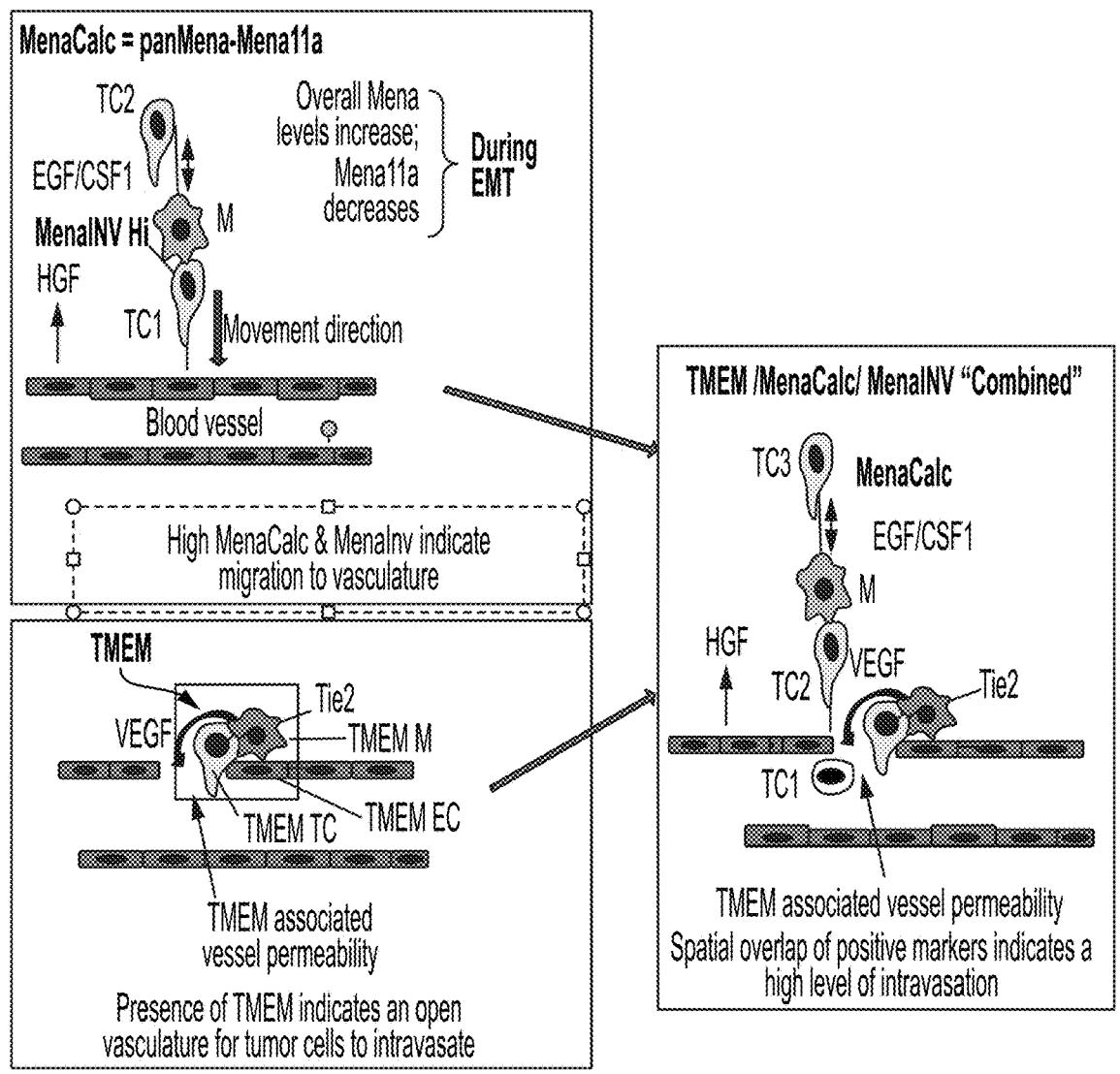
FIG. 1
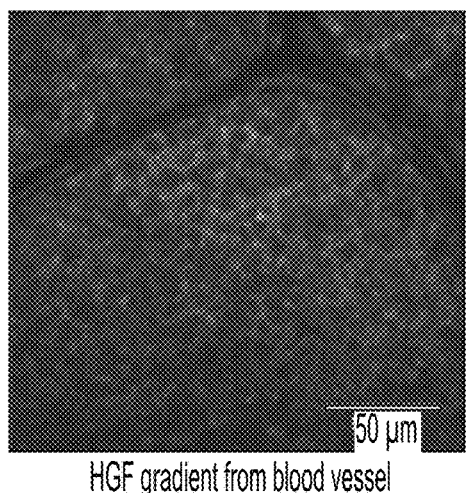
HGF gradient from blood vessel
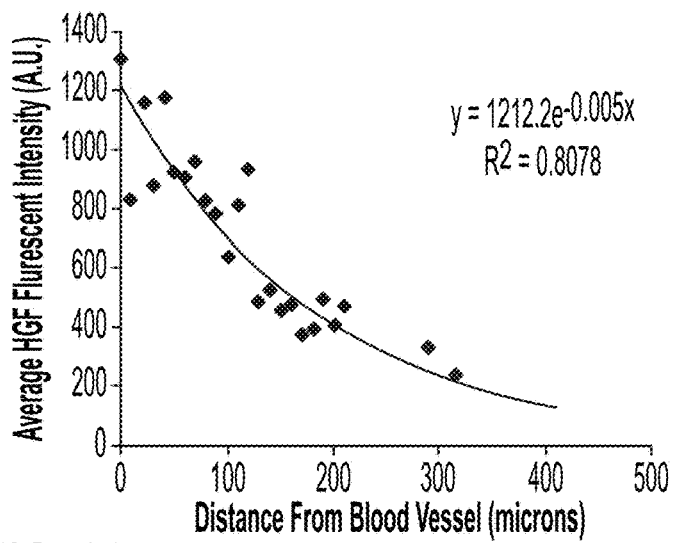
FIG. 2A

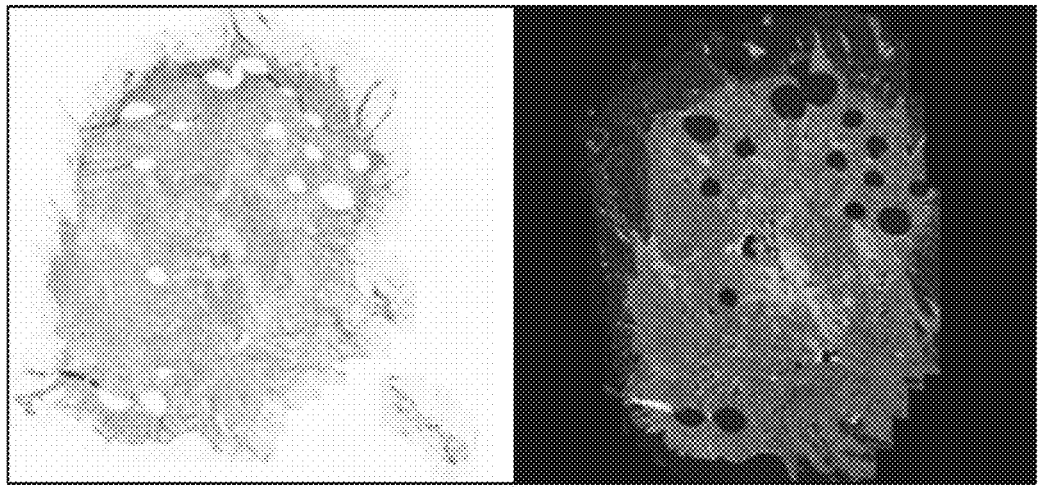
FIG. 4A            FIG. 4B
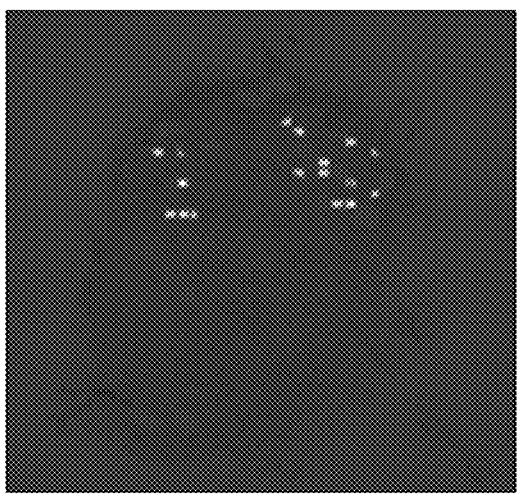    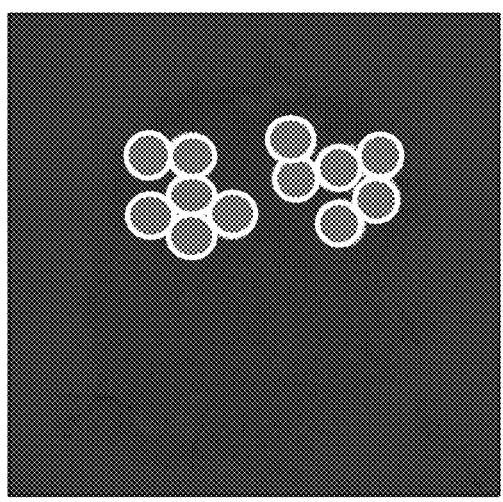
FIG. 4C            FIG. 4D

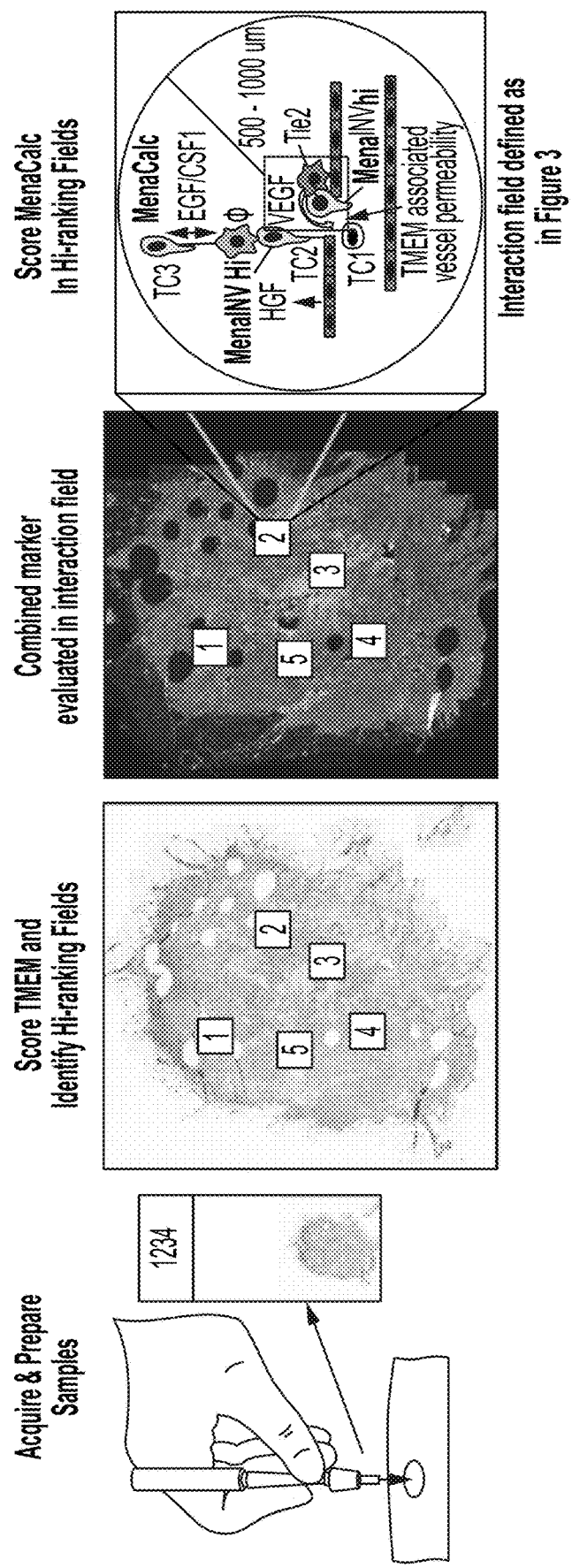

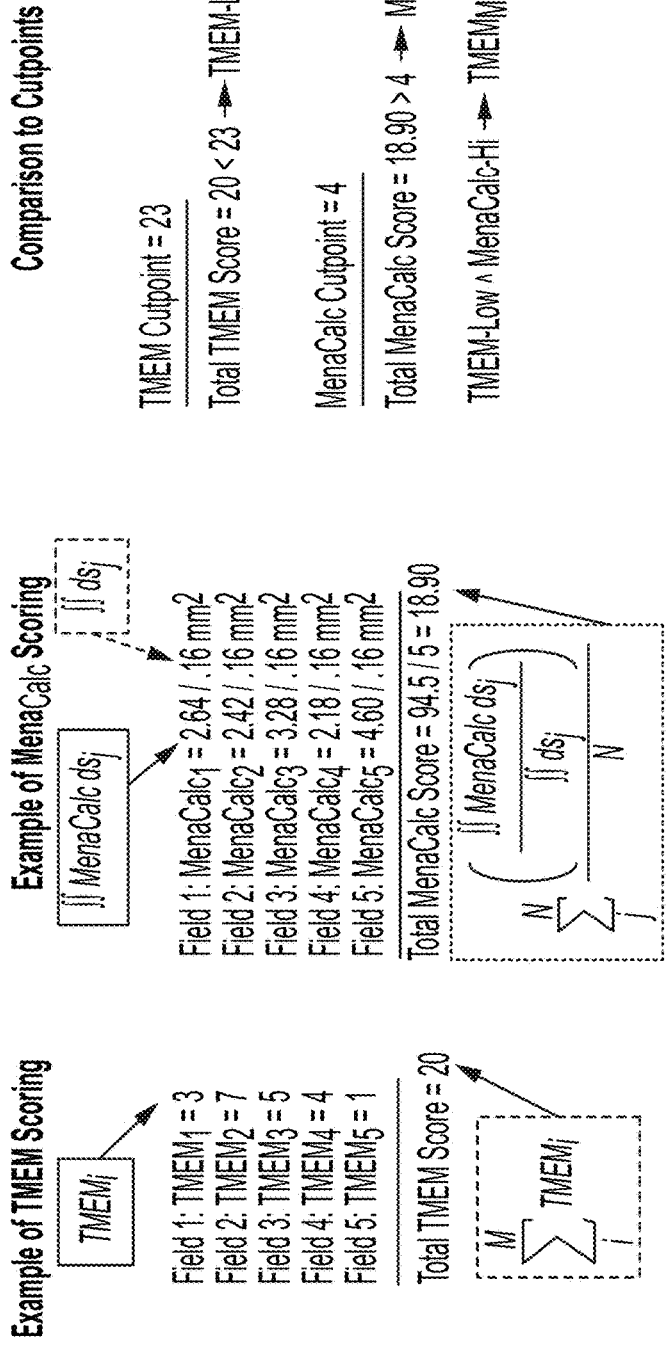

$$TMEM_{MenaCalc} = \underbrace{\left(\sum_{i}^{M} TMEM_i > TMEM_{cut}\right)}_{\text{TMEM Score}} \wedge \underbrace{\left(\sum_{j}^{N} \frac{\left(\frac{\iint MenaCalc \, ds_j}{\iint ds_j}\right)}{N} > MenaCalc_{cut}\right)}_{\text{MenaCalc Score}}$$

FIG. 9A $$TMEM_{MenaINV} = \underbrace{\left(\sum_{i}^{M} TMEM_i > TMEM_{cut}\right)}_{\text{TMEM Score}} \wedge \left(\sum_{j}^{N} \frac{\left(\frac{\iint MenaINV \, ds_j}{\iint ds_j}\right)}{N} > MenaINV_{cut}\right)$$

FIG. 9B $$\frac{TMEM_{MenaCalc}(drug)}{TMEM_{MenaCalc}(no\ drug)} \quad \text{and} \quad \frac{TMEM_{MenaINV}(drug)}{TMEM_{MenaINV}(no\ drug)}$$

FIG. 9C $$TMEM_{MenaCalc} = \frac{A\left(\sum_{i}^{M} TMEM_i\right) + B\left(\sum_{j}^{N} \frac{\left(\frac{\iint MenaCalc \, ds_j}{\iint ds_j}\right)}{N}\right)}{A+B}$$

$$TMEM_{MenaINV} = \frac{A\left(\sum_{i}^{M} TMEM_i\right) + B\left(\sum_{j}^{N} \frac{\left(\frac{\iint MenaINV \, ds_j}{\iint ds_j}\right)}{N}\right)}{A+B}$$

$$TMEM_{MenaCalc} = \frac{A\left(\sum_{i}^{N} TMEM_i\right) + B\left(\sum_{j}^{N} \frac{\left(\frac{\iint MenaCalc \, ds_j}{\iint ds_j}\right)}{N}\right)}{A+B}$$

$$TMEM_{MenaINV} = \frac{A\left(\sum_{i}^{N} TMEM_i\right) + B\left(\sum_{j}^{N} \frac{\left(\frac{\iint MenaINV \, ds_j}{\iint ds_j}\right)}{N}\right)}{A+B}$$

FIG. 10

$$TMEM_{MenaCalc} = \frac{A\left(\sum_{i}^{N} TMEM_i\right) + B\left(DDCtMenaCalc\right)/DDCtGAPDH}{A+B}$$

FIG. 11

SEQUENCE LISTING

```
<160> NUMBER OF SEQ ID NOS: 6

<210> SEQ ID NO 1
<211> LENGTH: 4
<212> TYPE: PRT
<213> ORGANISM: Homo sapiens

<400> SEQUENCE: 1

Phe Tyr Leu Gly
1
```

```
<210> SEQ ID NO 2
<211> LENGTH: 19
<212> TYPE: PRT
<213> ORGANISM: Homo sapiens

<400> SEQUENCE: 2

Ala Gln Ser Lys Val Thr Ala Thr Gln Asp Ser Thr Asn Leu Arg Cys
1               5                   10                  15

Ile Phe Cys

<210> SEQ ID NO 3
<211> LENGTH: 21
<212> TYPE: PRT
<213> ORGANISM: Homo sapiens

<400> SEQUENCE: 3

Arg Asp Ser Pro Arg Lys Asn Gln Ile Val Phe Asp Asn Arg Ser Tyr
1               5                   10                  15

Asp Ser Leu His Arg
            20

<210> SEQ ID NO 4
<211> LENGTH: 12
<212> TYPE: DNA
<213> ORGANISM: Homo sapiens

<400> SEQUENCE: 4
ttctatttag gg                                                       12

<210> SEQ ID NO 5
<211> LENGTH: 57
<212> TYPE: DNA
<213> ORGANISM: Homo sapiens

<400> SEQUENCE: 5
gcccagagca aggttactgc tacccaggac agcactaatt tgcgatgtat tttctgt      57

<210> SEQ ID NO 6
<211> LENGTH: 63
<212> TYPE: DNA
<213> ORGANISM: Homo sapiens

<400> SEQUENCE: 6
acgggattct ccaaggaaaa atcagattgt ttttgacaac aggtcctatg attcattaca   60
cag                                                                 63
```

COMBINED MARKERS FOR METASTATIC CANCER AND USES THEREOF

CROSS REFERENCE TO RELATED APPLICATIONS

This application claims the benefit of U.S. Provisional Application No. 62/607,438, filed on Dec. 19, 2017, the contents of which are hereby incorporated by reference.

STATEMENT OF GOVERNMENT SUPPORT

This invention was made with government support under grant numbers CA100324 and CA150344 awarded by the National Institutes of Health. The government has certain rights in the invention.

BACKGROUND OF THE INVENTION

Throughout this application various publications are referred to in parentheses. Full citations for these references may be found at the end of the specification. The disclosures of all publications, patents and patent applications mentioned herein are hereby incorporated by reference in their entirety into the subject application to more fully describe the art to which the subject invention pertains.

Multiphoton-based intravital imaging has demonstrated that invasive carcinoma cells in human, mouse and rat mammary tumors intravasate only when associated with TMEM (Tumor Microenvironment of Metastasis). TMEM are found in primary tumors and their resulting metastases (Rohan et al. 2014, U.S. Pat. No. 8,642,277). TMEM count in the primary tumor is prognostic of risk of metastatic recurrence and survival in cancer patients, and is predictive of response to standard forms of chemotherapy. TMEM assembly and function is mechanistically linked to the expression pattern of Mena isoforms where total Mena expression minus the expression of the metastasis suppressor Mena11a (MenaCalc=all Mena−Mena11a) is associated with TMEM assembly. MenaCalc is independently predictive of metastatic recurrence and survival in breast cancer patients, and is predictive of response to standard forms of chemotherapy (Agarwal et al. 2012, Forse et al. 2015, Karagiannis et al. 2016).

In addition, the MenaINV isoform is associated with increased receptor tyrosine kinase (RTK) sensitivity and invadopodium assembly, two events linked to efficient TMEM function. MenaINV levels are associated with increased TMEM function and metastatic risk, and are predictive of the response to standard forms of chemotherapy (Roussos et al. 2011a,b, Karagiannis et al 2016, Eddy et al 2017, U.S. Pat. No. 8,603,738).

The present invention provides methods and tests using a combination of markers (TMEM, MenaCalc, and MenaINV) for hematogenous metastatic cancer with superior diagnostic, prognostic and predictive capabilities.

SUMMARY OF THE INVENTION

The present invention provides methods and assays for determining metastatic risk in many common clinical scenarios. Two combined markers (TMEM$_{MenaCalc}$ and TMEM$_{MenaINV}$) are disclosed that serve as tests for hematogenous dissemination of tumor cells (metastasis) either at the time of first presentation, or later in treatment and act to predict progression to metastasis and identify patients who will benefit from aggressive anti-proliferation treatment (chemo- and radiation), including inhibitors of receptor tyrosine kinases (RTKs) and tyrosine kinases (TKs).

BRIEF DESCRIPTION OF THE DRAWINGS

FIG. 1. Summary model of individual markers for metastasis and their combination. Top left: High MenaCalc levels are indicative of increased tumor cell motility and invasion. Epithelial-mesenchymal transition (EMT) leads to an overall increase in Mena expression along with a switch in Mena isoform expression away from the metastasis-suppressing Mena11a. Simultaneous measurement of Mena11a (e.g. using Mena11a-specific antibodies) and all Mena isoforms (using Pan-Mena antibodies which also stains MenaINV, a prometastatic Mena isoform) allows the calculation of MenaCalc for the tissue, where MenaCalc=panMena (minus) Mena11a. MenaCalc-Hi tumor cells (TC) and macrophages (M) pair utilizing the colony stimulating factor 1/epidermal growth factor (CSF1/EGF) paracrine loop and stream uni-directionally towards endothelial cells (EC) that attract tumor cells by secreting hepatocyte growth factor (HGF) (Leung et al 2016). TC contact with M induces MenaINV expression (Pignatelli et al 2016). Bottom left: TMEM are responsible for opening the vasculature for tumor cell intravasation (Harney et al 2015). Perivascular Tie2-Hi-macrophages interact with perivascular tumor cells (TC) leading to invasion of the blood vessel wall by TMEM-associated tumor cells. Either MenaCalc or TMEM score are predictive of recurrence (Karagiannis et al. 2016). TMEM is identified as the direct contact between an EC, Mena-Hi-TC and macrophage. Right: Combined marker. While either MenaCalc or TMEM score are predictive of recurrence, in regions of the tumor where both MenaCalc and TMEM are elevated, MenaINV levels will rise and MenaCalc-Hi tumor cells will be associated with TMEM resulting in the highest efficiency of tumor cell intravasation (TC1) thus predicting that the combined marker will have the highest prognostic value.

FIG. 2A-2C. (A) HGF secreted by endothelial cells forms a gradient (left panel). This HGF gradient extends out from blood vessels and recruits tumor cells within ~500 μm of the blood vessel (Leung et al. 2016). (B) Beyond 500 macrophage-dependent paracrine signaling recruits tumor cells into the HGF directional stream (out to 1000 μm). As tumor cells approach the blood vessels with TMEM their frequency of collision with macrophages (triangles) increases resulting in increased MenaINV expression near TMEM. (C) MenaINV score plotted as a function of distance from TMEM center. MenaINV expressing tumor cells are depleted very close to TMEM due to their rapid intravasation at TMEM (Harney et al 2015).

FIG. 4A-4D. Example of combined marker algorithm. Serial sections stained for (A) TMEM in immunohistochemistry and (B) MenaCalc or MenaINV, can be aligned down to the single cell level. (C) TMEM analysis of the entire tissue identifies the fields of view containing the highest TMEM count. (D) Analysis of MenaCalc or MenaINV in these highest ranked TMEM fields of view forms the combined marker. Example circles in (D) are 1 mm radius circles around TMEM high fields to illustrate the interaction zone described in FIG. 3.

FIG. 8A-8H. Example workflow for acquisition of a combined marker score using MenaCalc as an example. (A) Samples are acquired and processed into microscope slides stained appropriately for TMEM and MenaCalc. (B) The TMEM prepared slide is evaluated for TMEM count and the highest ranking N fields of view are identified (boxes numbered 1-5). (C) The MenaCalc prepared slide is evaluated to determine MenaCalc score within the highest ranked fields of view identified in B (boxes numbered 1-5). (D) Scoring MenaCalc in the highest TMEM ranked fields means both individual markers are evaluated in the interaction field defined in FIG. 3. (E) Example of how calculation of TMEM score is performed. The number of TMEM structures in each field of view is tallied. These values correspond to the individual TMEM scores referenced by the formula segment in the solid box. The scores taken from the highest N (e.g. 5) ranked fields of view are then summed. This calculates the formula segment in the dashed box. (F) Example of how calculation of the MenaCalc score is performed. The MenaCalc signal within the top TMEM ranked fields is integrated (formula segment in the solid box) over the interaction field defined in D. This signal is then normalized to the interaction area (formula segment in the dashed box). The individual MenaCalc scores are then summed together and divided by the number of fields of view (i.e. averaged together). This is indicated by the formula segment in the dotted box. (G) Finally the combined TMEM-MenaCalc score is determined by comparing both the TMEM and the MenaCalc scores to a predetermined cutpoint using a logical conjunction (Boolean AND) operation. (H) Complete mathematical formula used for the example shown in panels E-G. Alternatively, a numerical score for TMEM-MenaCalc (and for TMEM-MenaINV, FIG. 10) may be obtained by a numerical weighting of the TMEM and the MenaCalc scores (as illustrated in FIG. 8H for TMEM$_{MenaCalc}$). As with the cut-points, the numerical weighting factors will be determined by evaluating cohorts of patient samples retrospectively and may vary with cancer type and molecular sub-type.

FIG. 9A-9C. (A)-(B) show two combined marker scoring equations using the steps in FIG. 8; (A) TMEM$_{MenaCalc}$, (B) TMEM$_{MenaINV}$. (C) Example of combined markers described in (A) or (B) to assess response to drug treatment by dividing the weighted average score obtained under the influence of the drug TMEM$_{MenaCalc\ (drug)}$ by the score obtained without the drug TMEM$_{MenaCalc\ (no\ drug)}$.

FIG. 10. Examples of quantitative numerical scoring for TMEM$_{MenaCalc}$, and TMEM$_{MenaINV}$. A numerical score for TMEM$_{MenaCalc}$ TMEM$_{MenaINV}$ may be obtained by a numerical weighting of the TMEM and the MenaCalc or MenaINV scores as shown. As with the cut-points, the numerical weighting factors will be determined by evaluating cohorts of patient samples retrospectively and may vary with cancer type and molecular sub-type.

FIG. 11. Example of quantitative numerical scoring for TMEM$_{MenaCalc}$, where MenaCalc is scored in a blood sample and TMEM is scored in a tumor sample from the same patient.

DETAILED DESCRIPTION OF THE INVENTION

Figure 2B:
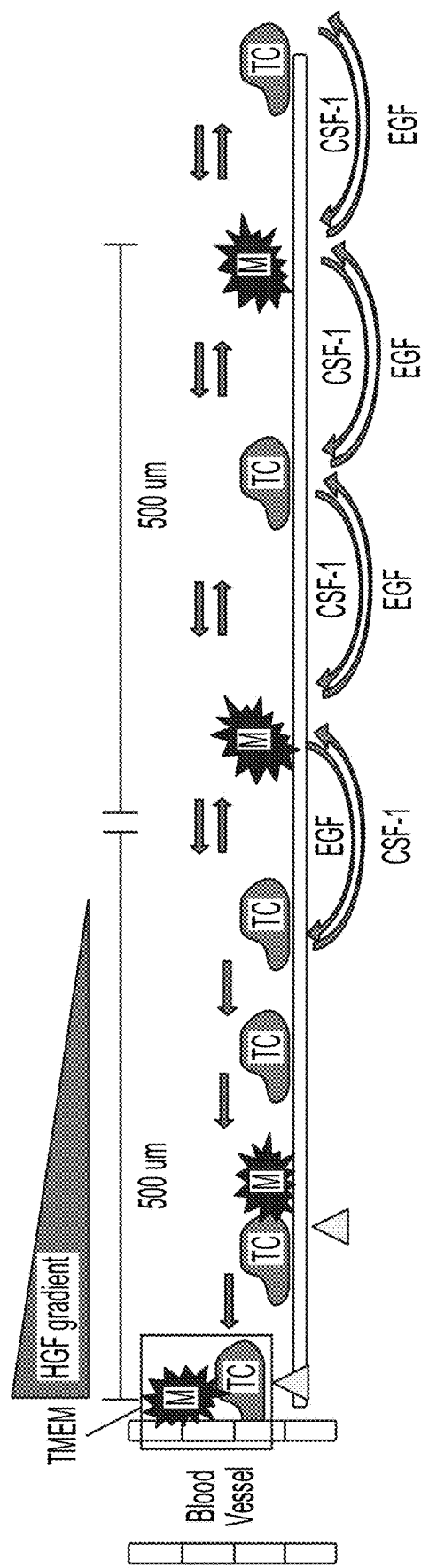

The invention provides a method for detecting a hematogenous metastatic cancer in a subject or detecting a likelihood of tumor cells from a subject undergoing hematogenous metastasis, as well as detecting their response to drugs designed to inhibit hematogenous metastasis, the method comprising
  i) obtaining a cancer tissue sample stained for the presence of macrophages, endothelial cells, and one or more of pan-Mena, MenaINV and Mena11a;
  ii) identifying regions of tumor microenvironment of metastasis (TMEM) within the tissue sample, wherein a TMEM is defined by:

(a) juxtaposition of a macrophage, an endothelial cell and an invasive tumor cell, wherein an invasive tumor cell is identified by expression of high pan-Mena, MenaCalc and/or MenaINV; or (b) Tie2Hi/VEGFHi macrophage in direct contact with a blood vessel with decreased VE-Cadherin and/or ZO-1 endothelial staining;

iii) determining if the sample has a High or Low TMEM Score, where the TMEM Score is High if the TMEM count in a number (N) fields of view is above a predetermined threshold (TMEMcut) and the TMEM Score is Low if the TMEM count in a number (N) fields of view is equal to or below a predetermined threshold (TMEMcut) and;

iv) performing within a specified distance from TMEM, in the highest ranked TMEM fields of view, a determination of one or both of
   a) levels of MenaINV, or
   b) levels of pan-Mena and Mena11a, and for b), calculating MenaCalc, where MenaCalc equals levels of pan-Mena minus levels of Mena11a;

v) determining if
   a) the sample has a High or a Low MenaINV Score, where the MenaINV Score is High when the MenaINV score in the highest ranked TMEM fields of view is above a predetermined threshold (MenaINVcut) and where the MenaINV Score is Low when the MenaINV score in the highest ranked TMEM fields of view is equal to or below a predetermined threshold (MenaINVcut), and/or
   b) the sample has a High or a Low MenaCalc Score, where the MenaCalc Score is High when the MenaCalc score in the highest ranked TMEM fields of view is above a predetermined threshold (MenaCalccut) and where the MenaCalc Score is Low when the MenaCalc score in the highest ranked TMEM fields of view is equal to or below a predetermined threshold (MenaCalc cut); and vi) detecting a hematogenous metastatic cancer in the subject or detecting a likelihood of tumor cells from the subject undergoing hematogenous metastasis if the sample has
   a) both a High TMEM Score and High MenaINV Score, and/or
   b) both a High TMEM Score and High MenaCalc Score;

wherein the presence of a Low TMEM Score and/or Low MenaINV Score, or the presence of a Low TMEM Score and/or Low MenaCalc Score indicates that the subject does not have a hematogenous metastatic cancer or does not have a likelihood of tumor cells undergoing hematogenous metastasis.

The invention also provides a method for detecting a hematogenous metastatic cancer in a subject or detecting a likelihood of tumor cells from a subject undergoing hematogenous metastasis, the method comprising:
   obtaining a sample of a cancer;
   staining the sample to identify presence of TMEM;
   applying image analysis to the sample stained for TMEM and quantifying the TMEM distribution in the sample;
   determining if a number (N) of different regions of TMEM distribution in the sample (TMEMi) are (i) above a predetermined threshold of TMEM distribution (TMEMcut) so as to obtain a High TMEM score or (ii) equal to or below a predetermined threshold of TMEM distribution (TMEMcut) so as to obtain a Low TMEM score, wherein a Low TMEM score indicates that the subject does not have a hematogenous metastatic cancer or does not have a likelihood of tumor cells undergoing hematogenous metastasis;
   if the TMEM score is High, determining a spatial center for each of the number of different regions of TMEM distribution in the sample that are above a predetermined threshold;
   staining the sample for the presence of MenaINV or for the presence of pan-Mena and Mena11a;
   applying image analysis to the sample stained for MenaINV or pan-Mena and Mena11a, and quantifying MenaINV or pan-Mena and Mena11a within a predetermined area centered on each of the spatial centers (MenaINV or MenaCalc, respectively) of the N different regions of TMEM, wherein MenaCalc=pan-Mena quantified minus Mena11a quantified;
   normalizing the MenaINV or MenaCalc values for the predetermined area size;
   determining if the total normalized MenaINV (i) is above a predetermined value (MenaINVcut) so as to obtain a High MenaINV score or (ii) equal to or below the MenaINVcut so as to obtain a Low MenaINV score; and/or determining if the total normalized MenaCalc (i) is above a predetermined value (MenaCalc cut) so as to obtain a High MenaCalc score or (ii) equal to or below the MenaCalc cut so as to obtain a Low MenaCalc score; and
   detecting a hematogenous metastatic cancer in the subject or detecting a likelihood of tumor cells from the subject undergoing hematogenous metastasis if the sample has
      a) both a High TMEM Score and High MenaINV Score, and/or
      b) both a High TMEM Score and High MenaCalc Score;

wherein the presence of a Low TMEM Score and/or Low MenaINV Score, or the presence of a Low TMEM Score and/or Low MenaCalc Score indicates that the subject does not have a hematogenous metastatic cancer or does not have a likelihood of tumor cells undergoing hematogenous metastasis.

The cancer tissue sample can be any cancer tissue sample, for example, a breast, pancreas, prostate, colon, brain, liver, lung, head or neck tumor sample. The tumor can be, for example, a secretory epithelial tumor. The patient can be estrogen receptor (ER)+ or ER−.

The TMEM score and the MenaINV Score or MenaCalc Score can be obtained, respectively, from serial sections of the sample which are aligned or co-registered. Alternatively, the TMEM score and the MenaINV Score or MenaCalc Score can be obtained, respectively, from the same section of the sample.

Multiplex staining can be used to stain TMEM, and MenaINV or pan-Mena & Mena11a. Endothelial cells can be detected, for example, using an agent that is specific for CD31. Macrophages can be detected, for example, using an agent specific for CD68, Tie2 and/or CD206. Invasive tumor cells can be detected, for example, using an agent specific for panMena or MenaINV.

The endothelial cells, macrophages, and/or invasive tumor cells can be detected using antibodies, monoclonal antibodies, antibody fragments, peptides, aptamers and/or cDNA probes that are specific for their target.

As used herein, the term "antibody" encompasses whole antibodies and fragments of whole antibodies wherein the fragments specifically bind to endothelial cells, macrophages, panMena, MenaINV or Mena11a. Antibody fragments include, but are not limited to, F(ab')2 and Fab' fragments and single chain antibodies. F(ab')2 is an antigen binding fragment of an antibody molecule with deleted crystallizable fragment (Fc) region and preserved binding region. Fab' is ½ of the F(ab')2 molecule possessing only ½ of the binding region. The term antibody is further meant to encompass polyclonal antibodies and monoclonal antibodies. Antibodies may be produced by techniques well known to those skilled in the art. Polyclonal antibody, for example, may be produced by immunizing a mouse, rabbit, or rat with purified polypeptides encoded by the variants of Mena. Monoclonal antibody may then be produced by removing the spleen from the immunized mouse, and fusing the spleen cells with myeloma cells to form a hybridoma which, when grown in culture, will produce a monoclonal antibody. The antibody can be, e.g., any of an IgA, IgD, IgE, IgG, or IgM antibody. The IgA antibody can be, e.g., an IgA1 or an IgA2 antibody. The IgG antibody can be, e.g., an IgG1, IgG2, IgG2a, IgG2b, IgG3 or IgG4 antibody. A combination of any of these antibodies subtypes can also be used. One consideration in selecting the type of antibody to be used is the size of the antibody. For example, the size of IgG is smaller than that of IgM allowing for greater penetration of IgG into tissues. The antibody can be a human antibody or a non-human antibody such as a goat antibody or a mouse antibody. Antibodies can be "humanized" using standard recombinant DNA techniques.

Human Mena sequences are indicated below:

```
Mena ++        FYLG
               (SEQ ID NO: 1),
               ttctatttag gg
               (SEQ ID NO: 4);

MenaINV        AQSKVTATQD STNLRCIFC
               (SEQ ID NO: 2),
               gcccagagca aggttactgc tacccaggac
               agcactaatt tgcgatgtat tttctgt
               (SEQ ID NO: 5);

Mena11a        RDSPRKNQIV FDNRSYDSLH R
               (SEQ ID NO: 3),
               acgggattct ccaaggaaaa atcagattgt
               ttttgacaac aggtcctatg attcattaca
               cag
               (SEQ ID NO: 6).
```

Aptamers are single stranded oligonucleotides or oligonucleotide analogs that bind to a particular target molecule, such as a protein. Thus, aptamers are the oligonucleotide analogy to antibodies. However, aptamers are smaller than antibodies. Their binding is highly dependent on the secondary structure formed by the aptamer oligonucleotide. Both RNA and single stranded DNA (or analog) aptamers can be used. Aptamers that bind to virtually any particular target can be selected using an iterative process called SELEX, which stands for Systematic Evolution of Ligands by EXponential enrichment.

The agent that specifically binds to macrophages, endothelial cells, panMena, MenaINV or Mena11a can be labeled with a detectable marker. Labeling may be accomplished using one of a variety of labeling techniques, including peroxidase, chemiluminescent, and/or radioactive labels known in the art. The detectable marker may be, for example, a nonradioactive or fluorescent marker, such as biotin, fluorescein (FITC), acridine, cholesterol, or carboxy X rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as, for example, $^{35}S$, $^{32}P$, or $^{3}H$. Radioactivity emitted by the radioisotope can be detected by techniques well known in the art. For example, gamma emission from the radioisotope may be detected using gamma imaging techniques, particularly scintigraphic imaging.

The expression of Mena can be normalized relative to the expression of protein variants that are not changed in expression in a metastatic tumor. Examples of proteins that could be used as controls include those of the Ena/VASP family that are unchanged in their expression in metastatic cells. Other examples of proteins or genes that could be used as controls include those listed as relatively unchanged in expression in disseminating tumor cells (Condeelis et al. 2005; Patsialou et al 2012). Such controls include N-WASP, Rac1, Pak1, and PKCalpha and beta.

A TMEM can be defined, for example, by juxtaposition of a macrophage, an endothelial cell and an invasive tumor cell, wherein an invasive tumor cell is identified by expression of high pan-Mena, MenaCalc and/or MenaINV (see, e.g., U.S. Pat. No. 8,642,277 B2).

A TMEM can also be defined, for example, by a Tie2Hi/VEGFHi (e.g., VEGFAHi) macrophage in direct contact with a blood vessel with decreased VE-Cadherin and/or ZO-1 endothelial staining (see, e.g., PCT International Publication No. WO 2016/19140).

The specified distance from TMEM regions used in the methods is preferably within a 1 mm radius of the TMEM regions. Preferably, the specified distance from TMEM regions is not less than a 500 μm radius of the TMEM regions. The predetermined area can be, for example, within a radius of from 500 μm to 1 mm of the spatial center of regions of TMEM distribution in the sample which are above the predetermined threshold.

In one embodiment, staining the sample to identify the presence of TMEM, and staining the sample for the presence of MenaINV or for the presence of pan-Mena and Mena11a are preferably performed prior to determining a spatial center for each of the number of different regions of TMEM distribution in the sample that are above a predetermined threshold. In one embodiment, an image of the sample stained for TMEM and an image of the sample stained for pan-Mena and Mena11a are aligned to a single cell level prior to applying image analysis to the sample stained for TMEM and quantifying the TMEM distribution in the sample or prior to determining a number (N) of different regions of TMEM distribution in the sample (TMEMi) which are above a predetermined threshold of TMEM distribution (TMEMcut).

In one embodiment, a $TMEM_{MenaINV}$ Score is calculated by:

$$TMEM_{MenaINV} = \left(\sum_{i}^{M} TMEM_i > TMEM_{cut}\right) \wedge \left(\sum_{j}^{N} \frac{\left(\frac{\int\int MenaINV\, ds_j}{\int\int ds_j}\right)}{N} > MenaINV_{cut}\right).$$

In one embodiment, a $TMEM_{MenaCalc}$ Score is calculated by:

$$TMEM_{MenaCalc} = \left(\sum_{i}^{M} TMEM_i > TMEM_{cut}\right) \wedge$$

-continued $$\left(\sum_{j}^{N}\frac{\left(\frac{\int\int MenaCalc\,ds_j}{\int\int ds_j}\right)}{N}>MenaCalc_{cut}\right).$$

In one embodiment, a $TMEM_{MenaCalc}$ Score is calculated by:

$$TMEM_{MenaCalc}=\frac{A\left(\sum_{i}^{M}TMEM_i\right)+B\left(\sum_{j}^{N}\frac{\left(\frac{\int\int MenaCalc\,ds_j}{\int\int ds_j}\right)}{N}\right)}{A+B}.$$

In one embodiment, a $TMEM_{MenaINV}$ Score is calculated by:

$$TMEM_{MenaINV}=\frac{A\left(\sum_{i}^{M}TMEM_i\right)+B\left(\sum_{j}^{N}\frac{\left(\frac{\int\int MenaINV\,ds_j}{\int\int ds_j}\right)}{N}\right)}{A+B}.$$

Examples of formulae for the analysis of the combined markers are presented below. In (A) the $TMEM_{MenaCalc}$ score is composed of the Boolean comparison of the two individual markers, TMEM Score and MenaCalc Score ($\wedge$=Boolean AND). TMEM Score is categorized as High if the sum of the TMEM Count in N fields of view is above a predetermined threshold ($TMEM_{cut}$) (>=Boolean comparison). The MenaCalc Score is categorized as High if the average of the MenaCalc fluorescence signal (MenaCalc) over the highest ranking TMEM interaction fields of view is greater than a predetermined MenaCalc signal threshold ($MenaCalc_{cut}$). The double integral within the MenaCalc Score summation indicates the total sum of the MenaCalc signal over the entire field of view's area, normalized to the area of that field of view ($ds_j$ is the infinitesimal area of integration). Both thresholds, $TMEM_{cut}$ and $MenaCalc_{cut}$, may be different for each tumor type and can be tuned to adjust the sensitivity and specificity of each test. In (B) $TMEM_{MenaINV}$ is a similar analysis replacing the MenaCalc with MenaINV fluorescence signals and thresholds. The combined marker can also be expressed as a continuous measurement by taking the weighted average of the TMEM and MenaCalc scores as shown for $TMEM_{MenaCalc}$ in (C). A similar formula can be written for $TMEM_{MenaINV}$. See also FIG. 10. The weighting factors A & B may be different for each tumor type and can be tuned to adjust the sensitivity and specificity of the combined marker. In (D) combined markers described in equations A or B are used to assess response to drug treatment by dividing the weighted average score obtained under the influence of the drug $TMEM_{MenaCalc\,(drug)}$ by the score obtained without the drug $TMEM_{MenaCalc\,(no\,drug)}$. The drug can be, for example, a cytotoxic chemotherapy, receptor tyrosine kinase (RTK) inhibitor, TK inhibitor or combinations thereof.

$$TMEM_{MenaCalc}=\underbrace{\left(\sum_{i}^{M}TMEM_i>TMEM_{cut}\right)}_{TMEM\,Score}\wedge \qquad A$$

$$\underbrace{\left(\sum_{j}^{N}\frac{\left(\frac{\int\int MenaCalc\,ds_j}{\int\int ds_j}\right)}{N}>MenaCalc_{cut}\right)}_{MenaCalc\,Score}$$

$$TMEM_{MenaINV}=\left(\sum_{i}^{M}TMEM_i>TMEM_{cut}\right)\wedge \qquad B$$

$$\left(\sum_{j}^{N}\frac{\left(\frac{\int\int MenaINV\,ds_j}{\int\int ds_j}\right)}{N}>MenaINV_{cut}\right)$$

$$TMEM_{MenaCalc}=\frac{A\left(\sum_{i}^{M}TMEM_i\right)+B\left(\sum_{j}^{N}\frac{\left(\frac{\int\int MenaCalc\,ds_j}{\int\int ds_j}\right)}{N}\right)}{A+B}$$

$$\frac{TMEM_{MenaCalc\,(drug)}}{TMEM_{MenaCalc\,(no\,drug)}}\text{ and }\frac{TMEM_{MenaINV\,(drug)}}{TMEM_{MenaINV\,(no\,drug)}} \qquad C$$

Figure 3:
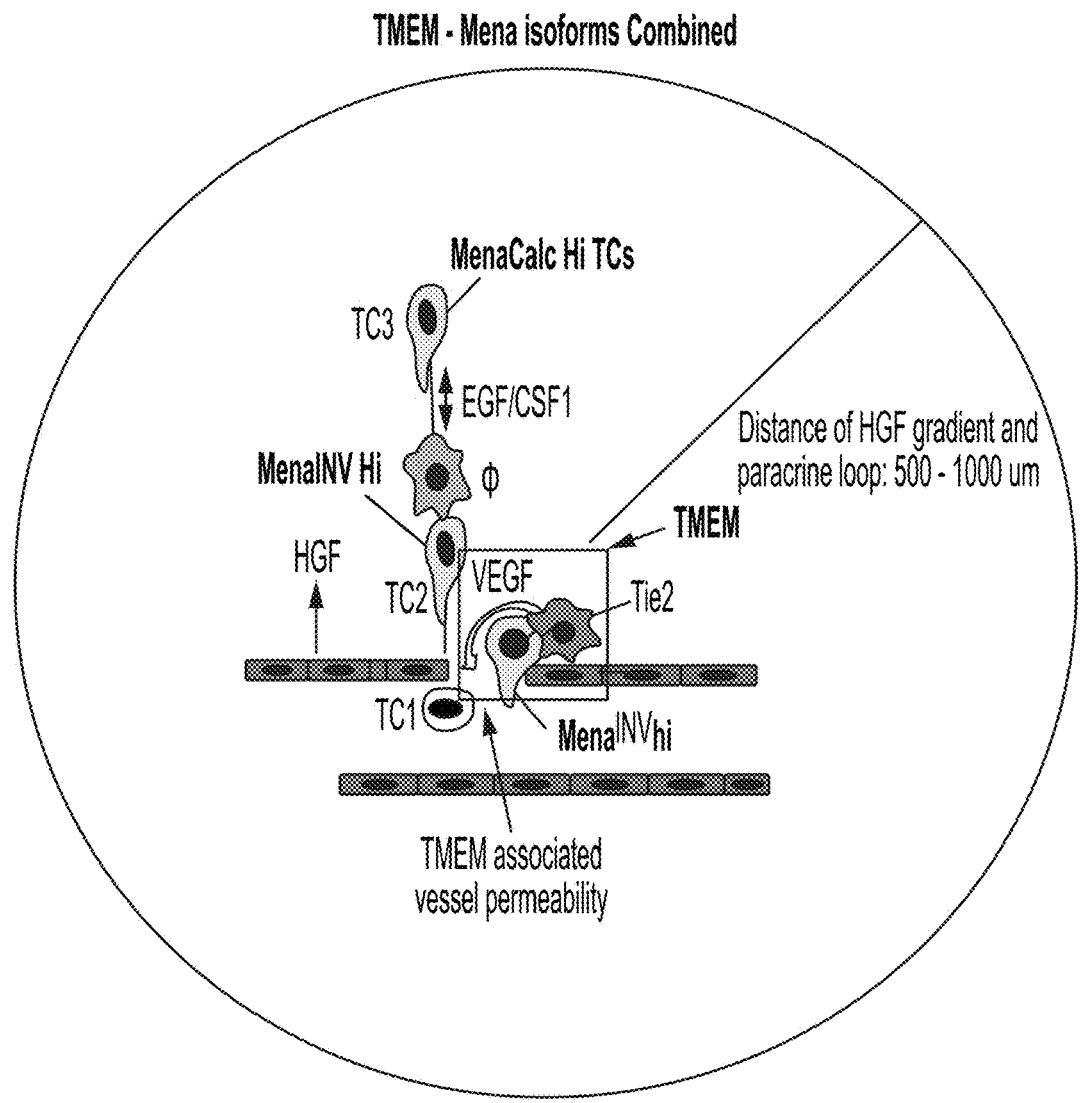
FIG. 3. Conceptual model for combined markers. While TMEM (central box) is the site of intravasation and hematogenous dissemination, efficient dissemination can only occur when there is a supply of migratory (MenaCalc-Hi, MenaINV-Hi) tumor cells in their vicinity. Analyzing the MenaCalc or MenaINV signals within a region that is defined by the distance of influence of the HGF gradient and paracrine loop as defined in FIG. 2 defines the TMEM—MenaCalc interaction zone and leads to the combined marker.

In one embodiment of the methods disclosed herein, TMEM is scored in a tumor tissue, and MenaCalc and/or MenaINV can be scored in a blood sample from the same subject to detect the Mena expression status of tumor cell intravasation e.g., FIG. 3). The equations disclosed herein can be used in the blood test version of the invention by changing the Area intensity integration terms used for MenaCalc and MenaINV to a simple numerical score based on signal intensity in the circulating tumor cells of a blood sample (not spatially specified) with cut points defined by a training set of blood samples from normal subjects.

The agent used to detect and score MenaCalc and or MenaINV levels can be, for example, one or more of an antibody, an antibody fragment, a peptide or an aptamer. An agent can also be a cDNA probe. In one formulation of this method qRT-PCR for Mena splice variants is performed as described previously (Pignatelli et al 2014). Briefly, MenaCalc and/or MenaINV levels are determined using the DDCt PCR method with cDNA primers specific to each Mena slice variant, and in which all MENA Ct values in the carcinoma samples are first normalized to glyceraldehyde 3-phosphate dehydrogenase (GAPDH). In this case for the MenaCalc example is shown as $$TMEM_{MenaCalc}=\frac{A\left(\sum_{i}^{N}TMEM_i\right)+B(DDCtMenaCalc)/DDCtGAPDH}{A+B}.$$

In one embodiment, intensity scores for MenaCalc and MenaINV are substituted in the existing equations with different terms defining the score for Mena isoforms in the tumor cell intravasation (TC1) population (FIG. 3) in blood samples from patients. In this version of the invention, the bloods can be drawn during neoadjuvant drug treatment before resection of the primary tumor (see Karagiannis et al.

2017). These blood sample scores are then combined with the TMEM score obtained either in a core biopsy from the patient taken before and during drug treatment or the TMEM score taken in the resected tumor after surgery. Intensity can be measured using, for example, fluorescence or PCR.

The invention also provides a method of assessing effectiveness of a treatment for metastatic cancer in a subject comprising
   a) obtaining a first TMEM Score and MenaINV Score and/or a first TMEM Score and MenaCalc Score by any of the methods disclosed herein before treatment of the subject or at a first stage of treatment of the subject;
   b) obtaining a second TMEM Score and MenaINV Score and/or a second TMEM Score and MenaCalc Score after treatment of the subject or at a second stage of treatment of the subject; and
   c) comparing the scores obtained in step a) and step b), wherein a decrease in the TMEM Score and/or MenaINV Score and/or a decrease in the TMEM Score and/or MenaCalc Score after treatment of the subject indicates that the treatment is effective in treating metastatic cancer or in decreasing the likelihood of a cancer to metastasize; and
   wherein an increase in the TMEM Score and/or MenaINV Score and/or an increase in the TMEM Score and/or MenaCalc Score indicates a need to continue treatment and/or switch to a different treatment.

The treatment can be, for example, a cytotoxic chemotherapy drug, a receptor tyrosine kinase (RTK) inhibitor, a (TK) tyrosine kinase inhibitor, or combinations thereof. The RTK inhibitor can be, for example, an EGFR, HGFR, IGFR, CSF1R, Tie2 or VEGFR inhibitor, or combinations thereof. The TK inhibitor can be, for example, a Src, Abl or Arg inhibitor, or combinations thereof. The treatment can comprise, for example, administration of rebastinib (4-[4-[(5-tert-butyl-2-quinolin-6-ylpyrazol-3-yl)carbamoylamino]-3-fluorophenoxy]-N-methylpyridine-2-carboxamide), an anti-tubulin chemotherapy, a taxane (e.g. paclitaxel), a non-taxane microtubule inhibitors (e.g. eribulin), a topoisomerase inhibitor (e.g. etoposide), an intercalating agent (e.g. doxorubicin), a DNA cross-linking agent (e.g. cisplatin), an alkylating agent (e.g. cyclophosphamide), or combinations thereof. The treatment can be, or comprise, radiation.

The invention also provides a method for assessing the prognosis of a subject undergoing treatment for a tumor, the method comprising obtaining a TMEM Score and MenaINV Score and/or a TMEM Score and MenaCalc Score by any of the methods disclosed herein at different time points during treatment, wherein an increase in the Score over time indicates a worsening of the subject's prognosis.

The invention further provides method for determining a course of treatment for a tumor for a subject, the method comprising obtaining a TMEM Score and MenaINV Score and/or a TMEM Score and MenaCalc Score by any of the methods disclosed herein, wherein both a High TMEM Score and High MenaINV Score, and/or both a High TMEM Score and High MenaCalc Score indicate that the subject is at increased risk of hematogenous metastasis and should be treated for a metastatic tumor or wherein a Low TMEM, Low MenaINV and/or Low MenaCalc Score indicates that the subject is at little risk of hematogenous metastasis and may not need to be treated for a metastatic tumor.

The invention also provides a method of treating a subject for a hematogenous metastatic cancer comprising
   a) receiving an indication that the subject has a hematogenous metastatic cancer or a likelihood of tumor cells undergoing hematogenous metastasis, wherein the subject was diagnosed by any of the methods disclosed herein; and
   b) administering an anti-cancer therapy to the subject identified as having a hematogenous metastatic cancer or a likelihood of tumor cells undergoing hematogenous metastasis.

The invention further provides a method of treating a patient comprising
   a) ordering a diagnostic test performed by any of the methods disclosed herein, and
   b) treating the patient based on the results of the diagnostic test;
   wherein a test result indicating that the patient has a hematogenous metastatic cancer or that tumor cells of the patient are likely undergoing hematogenous metastasis requires aggressive anti-cancer therapy.

The treatment or therapy can comprise, for example, one or more of a cytotoxic chemotherapy drug, a receptor tyrosine kinase (RTK) inhibitor, a (TK) tyrosine kinase inhibitor, an EGFR, HGFR, IGFR, CSF1R, Tie2 or VEGFR inhibitor, a Src, Abl or Arg inhibitor, rebastinib (4-[4-[(5-tert-butyl-2-quinolin-6-ylpyrazol-3-yl)carbamoylamino]-3-fluorophenoxy]-N-methylpyridine-2-carboxamide), an anti-tubulin chemotherapy, a taxane (e.g. paclitaxel), a non-taxane microtubule inhibitors (e.g. eribulin), a topoisomerase inhibitor (e.g. etoposide), an intercalating agent (e.g. doxorubicin), a DNA cross-linking agent (e.g. cisplatin), an alkylating agent (e.g. cyclophosphamide), radiation and surgery, or combinations thereof.

The invention also provides a method for screening for a candidate compound that inhibits metastasis of a tumor, the method comprising:
   obtaining a first TMEM Score and MenaINV Score and/or a first TMEM Score and MenaCalc Score using a cell line or tumor cells obtained from cancer patients (e.g., by fine needle aspiration) that express one or more of pan-Mena, MenaINV and Mena11a co-cultured in the presence of macrophages and endothelial cells to allow for TMEM self-assembly (e.g., using an in vitro sub-luminal-to-luminal transendothelial migration (TEM) [intravasation-directed TEM (iTEM)] assay; Pignatelli et al 2014, Harney et al 2017);
   contacting the compound with the cell line or tissue culture after TMEM self-assembly; and
   obtaining a second TMEM Score and MenaINV Score and/or a second TMEM Score and MenaCalc Score;
   wherein a reduction in the Score after treatment with the compound is indicative that the compound is a candidate compound for inhibiting metastasis of a tumor, and wherein lack of reduction in the Score is indicative that the compound is not a candidate compound for inhibiting metastasis.

In different embodiments of the methods disclosed herein, the TMEM Score, MenaINV Score, and/or MenaCalc Score are assigned a quantitative value.

The invention further provides a kit for detecting a hematogenous metastatic cancer and for determining the risk of tumor cells undergoing hematogenous metastasis comprising an agent that specifically binds to CD31 for detecting endothelial cells, an agent that specifically binds to CD68, Tie2 and/or CD206 for detecting macrophages, and one or more of an agent that specifically binds to panMena, an agent that specifically binds to MenaINV, and an agent that specifically binds to Mena11a. The agents can be, for example, antibodies, monoclonal antibodies, antibody fragments, peptides, aptamers, cDNA probes, or combinations thereof.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Overview

The present invention provides methods for using a combination of markers (TMEM, MenaCalc, and MenaINV) for hematogenous metastatic cancer for superior diagnostic, prognostic and predictive performance.

Examples

Figure 2C:
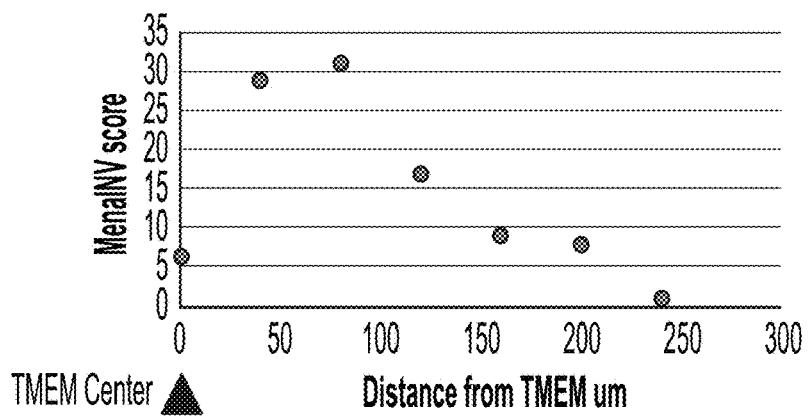

The results shown in FIG. 2 provide the basis for the development of the marker of the invention. Hepatocyte growth factor (HGF) secreted by endothelial cells forms a gradient which extends out from blood vessels and recruits tumor cells within ~500 µm of the blood vessel. However, beyond 500 µm (and out to 1000 µm), macrophage-dependent paracrine signaling recruits tumor cells into the HGF directional stream (Leung et al. 2016). As tumor cells approach the blood vessel their frequency of collision with macrophages (triangles) increases resulting in increased MenaINV expression (Pignatelli et al 2016).

As shown in FIG. 5, paclitaxel increases TMEMScore, MenaCalc and MenaINV expression in breast cancer patients treated with NAC (Karagiannis et al. 2017). FIG. 5A shows the study design. Individual TMEM scores of 20 patients were determined before and after receiving NAC, which included weekly paclitaxel (80 mg/m$^2$×12 consecutive weeks) followed sequentially by dose-dense AC chemotherapy (doxorubicin 60 mg/m$^2$ and cyclophosphamide 600 mg/m$^2$ every 2 weeks×4 cycles, plus pegrastim 6 mg SC on day 2 of each cycle) (see FIG. 5B). Horizontal line=TMEM high-risk cutoff point. The mean TMEMscores in these 20 human breast cancers before and after receiving NAC is shown in FIG. 5C (Wilcoxon test).

Figure 5A:
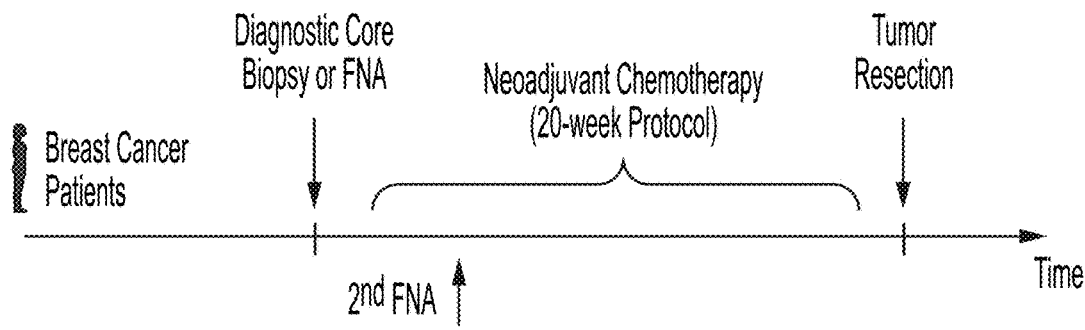
FIG. 5A-5D. Neoadjuvant chemotherapy increases TMEM, MenaCalc and MenaINV scores in some breast cancer patients. Paclitaxel (and other cytotoxic chemotherapy) increases TMEM Score, MenaCalc and MenaINV expression in breast cancer patients treated with neoadjuvant chemotherapy (NAC). (A) Study design. (B) Individual TMEM scores of 20 patients before and after receiving NAC, which included weekly paclitaxel (80 mg/m$^2$×12 consecutive weeks) followed sequentially by dose-dense AC chemotherapy (doxorubicin 60 mg/m$^2$ and cyclophosphamide 600 mg/m$^2$ every 2 weeks×4 cycles, plus pegrastim 6 mg SC on day 2 of each cycle). Horizontal line; TMEM high-risk cutoff point. For each pair of bars, Pre-NAC scores are shown in the first bar in the pair and Post-NAC scores are shown in the second bar. (C) Mean TMEMscores in the 20 human breast cancers shown in B, before and after receiving NAC (Wilcoxon test). (D) MenaCalc expression in fine needle aspiration (FNA) biopsies, as assessed by real-time RT-PCR from 4 patients before and after 2 doses of neoadjuvant chemotherapy with paclitaxel. (E) MenaINV gene expression in FNA biopsy samples, as assessed by real-time RT-PCR, taken from 5 breast cancer patients before and after 2-weeks of receiving NAC with paclitaxel. For each pair of bars, Pre-NAC scores are shown in the first bar in the pair and Post-NAC scores are shown in the second bar.
Figure 5B:
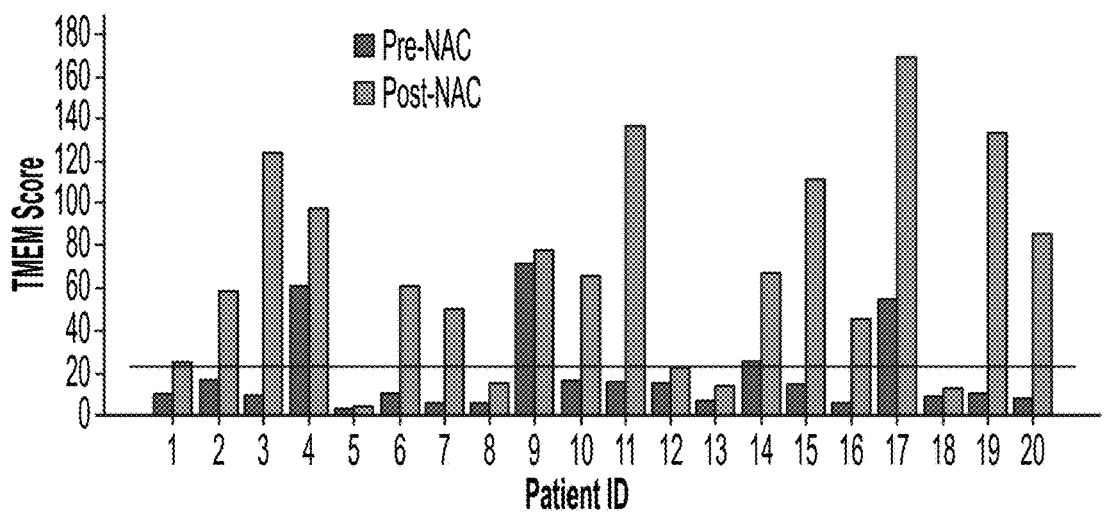
Figure 5C:
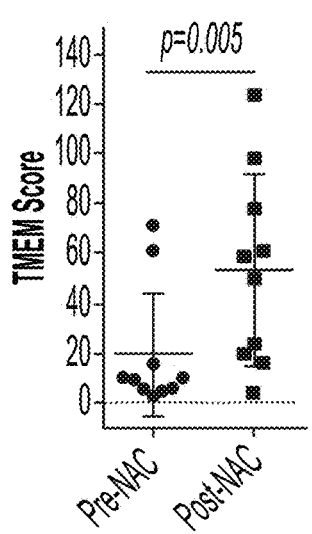
Figure 5D:
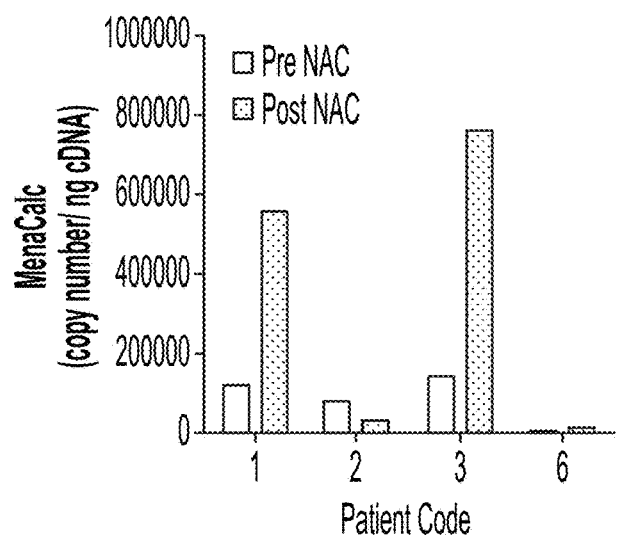
Figure 5E:
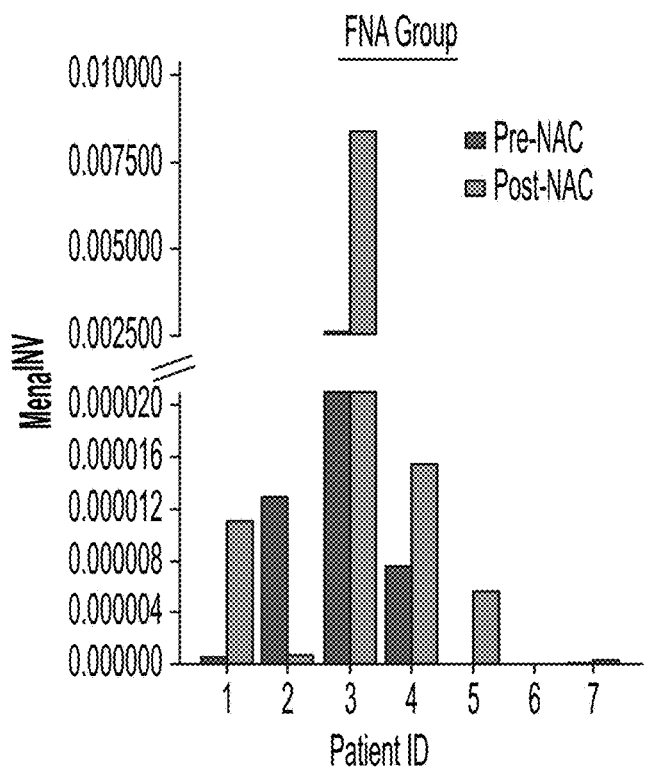

MenaCalc expression was determined in fine needle aspiration (FNA) biopsies, as assessed by real-time RT-PCR from 4 patients before and after 2 doses of neo-adjuvant chemotherapy with paclitaxel (see FIG. 5D). In addition, MenaINV gene expression was determined in FNA biopsy samples, as assessed by real-time RT-PCR, taken from 5 breast cancer patients before and after 2-weeks of receiving NAC with paclitaxel (see FIG. 5E) (Karagiannis et al. 2017).

Figure 6:
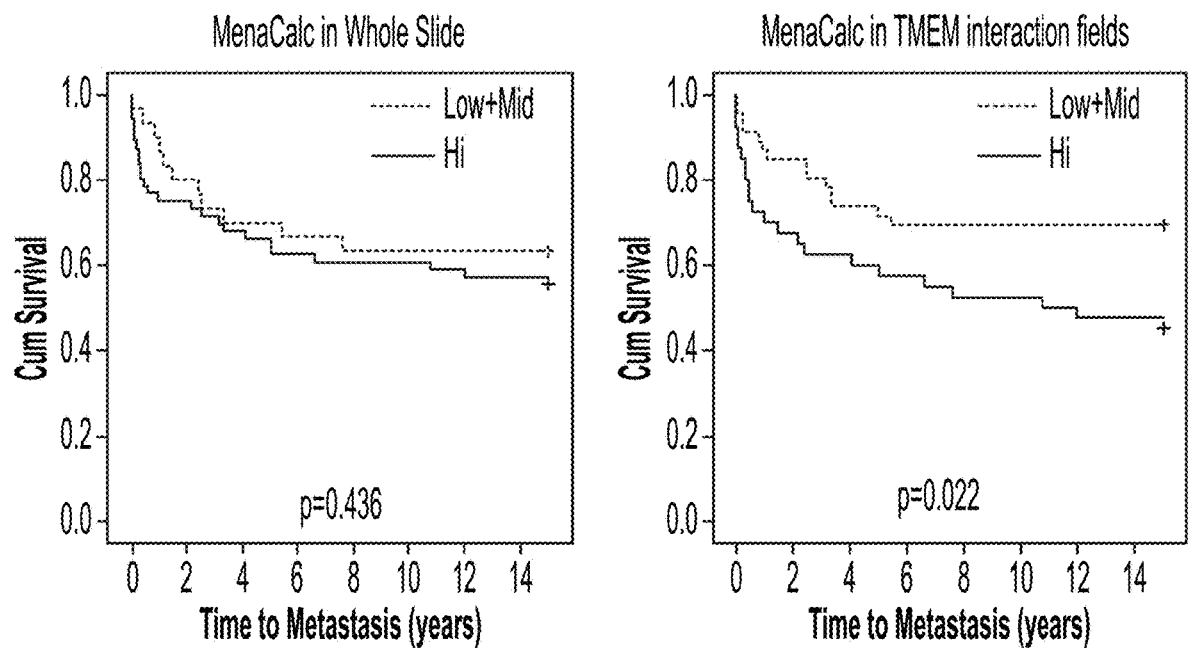
FIG. 6. Spatially aligned MenaCalc analysis outperforms traditional MenaCalc analysis in predicting 15 year metastasis free survival. Using outcome data for a cohort of 87 ER+ patients, the predictive performance of the traditional MenaCalc analysis (MenaCalc analyzed over the entire primary tumor) can be directly compared to the MenaCalc analysis evaluated only in the TMEM interaction fields detected here using automation to assign the top TMEM ranked fields. Low+Mid scores plot is above Hi scores plot in survival plots.
Figure 7A:
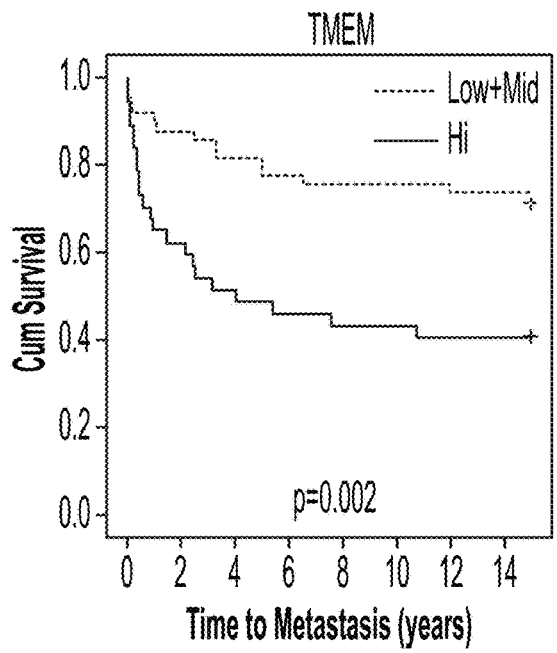
FIG. 7A-7D. The combined marker TMEM$_{MenaCalc}$ outperforms both the TMEM and TMEM field-associated MenaCalc analyses in predicting 15 year metastasis free survival. (A) 15 year metastasis free survival evaluated using TMEM score alone. Patients were stratified into two groups: Low+Mid scoring patients (top line) and High scoring patients (bottom line). (B) 15 year metastasis free survival evaluated using MenaCalc scored in the TMEM interaction fields (as in FIG. 6) in Low+Mid (top line) scoring patients and High (bottom line) scoring patients. (C) 15 year metastasis free survival evaluated using the combined marker. Patients were stratified into two groups: Low+Mid scoring patients (top line) and High scoring patients (bottom line). (D) 15 year metastasis free survival evaluated using the combined marker. Patients were stratified into four groups where the combined marker's TMEM and MenaCalc component scores were differentiated as: Curve 1=TMEM-Lo and MenaCalc-Lo; Curve 2=TMEM-Lo and MenaCalc-Hi; Curve 3=TMEM-Hi and MenaCalc-Lo; Curve 4=TMEM-Hi and MenaCalc-Hi.
Figure 7B:
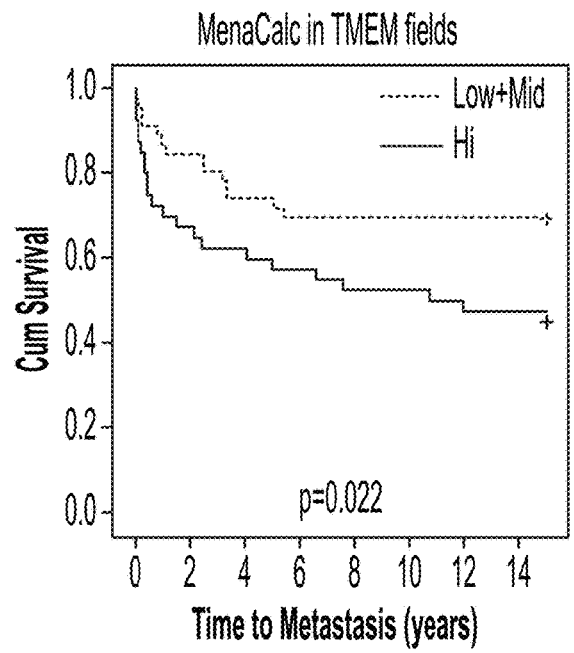
Figure 7C:
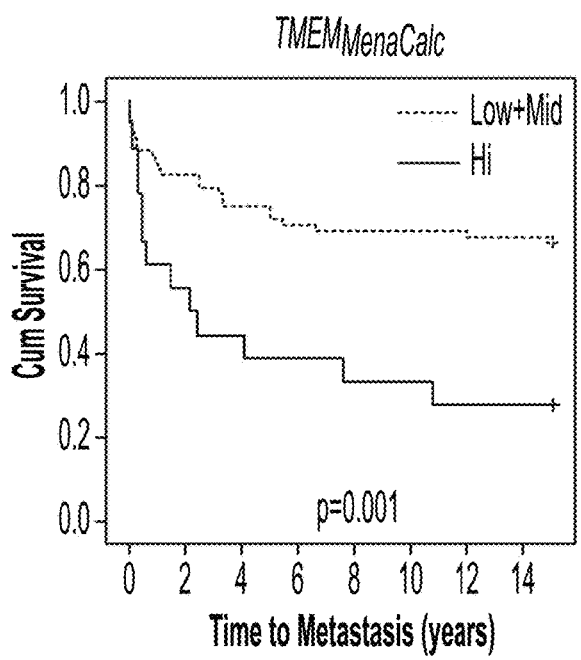
Figure 7D:
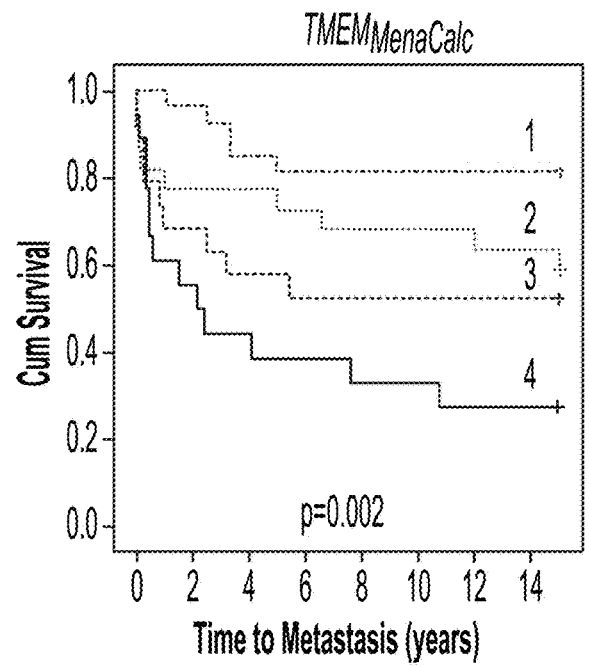

The results in FIG. 6 indicate that associating TMEM with MenaCalc by spatially aligning MenaCsalc analysis outperforms traditional MenaCalc analysis in predicting 15 year metastasis free survival. Indeed, we observed this improvement of predictive ability by using outcome data for a cohort of 87 ER+ patients and comparing the predictive performance of the traditional MenaCalc analysis (MenaCalc analysis over whole slide) to the MenaCalc analysis measured solely in the TMEM interaction fields (FIG. 6). Moreover, as shown in FIG. 7, the combined marker TMEM$_{MenaCalc}$ outperforms both the TMEM and TMEM field-associated MenaCalc analyses in predicting 15 year metastasis free survival. This is summarized in Table 1.

TMEM has been shown to be predictive of metastatic outcome in patients with ER+ disease, but this association has not held for patients with triple negative disease (Rohan et al. 2014). To address whether the combined marker can improve the predictive ability of TMEM in this subset of patients, cohorts of ER+ and ER− patients obtained from the New York Pathology Oncology Group were analyzed. The TMEM-MenaCalc combined marker was successfully able to predict metastatic outcomes in both the ER+ and ER− groups (Table 2).

TABLE 1

Superior performance of combined marker in predicting 15 year metastasis-free survival over TMEM or MenaCalc

| Test | Significance |
| --- | --- |
| TMEM | p = 0.002 |
| MenaCalc over whole slide | p = 0.436 |
| MenaCalc in TMEM Fields | p = 0.022 |
| TMEM$_{MenaCalc}$ | p = 0.001 |

TABLE 2

TMEM-MenaCalc combined marker predicts metastatic outcomes in the ER+ and ER− patient groups.

| TMEM in ER+ (Rohan et al. 2014) | TMEM in ER− (Rohan et al. 2014) | Combined Marker in ER+ (NYPOG) | Combined Marker in ER− (NYPOG) |
| --- | --- | --- | --- |
| p < 0.001 | p = 0.58 | p < 0.0001 | p = 0.012 |

Discussion

MenaCalc and TMEM, once formed, are relatively permanent features of the tumor microenvironment. MenaCalc increases during EMT (Karagiannis et al. 2016, Eddy et al. 2017). MenaINV is transiently induced in tumor cells by macrophage contact (Pignatelli et al. 2016). MenaCalc, MenaINV and TMEM are independently prognostic for metastatic risk (Karagiannis et al 2016). All markers are mechanistically linked meaning that Mena isoform changes are associated with TMEM assembly and function MenaINV expression resulting from macrophage contact increases RTK (EGFR, HGFR, IGFR, CSF1R) sensitivity to their ligands and resistance of tumor cells to RTK (EGFR, HGFR, IGFR, CSF1R, Tie2, VEGFR) and TK (Src, Abl, Arg) inhibitors (Eddy et al 2017).

Mena isoform expression and TMEM assembly and function are mechanistically linked. MenaCalc, MenaINV and TMEM are predictive of poor response to chemotherapy. MenaCalc and MenaINV have improved performance when evaluated in the TMEM interaction field. The combinations represented by either TMEM$_{MenaCalc}$ or TMEM$_{MenaInv}$ outperform the individual markers in both prognosis and prediction of response to drug treatment. These combinations, based upon the mechanistic interaction between, and spatial relationship of the individual markers, and/or the Mena isoform expression pattern of intravasated tumor cells associated with TMEM, is a non-conventional insight and represents the invention. TMEM$_{MenaCalc}$ combined marker test predicts risk of distant recurrence and survival. TMEM$_{MenaINV}$ combined marker indicates the extent to which the TMEM-MenaCalc interaction field is operating. The combinations represented by either TMEM$_{MenaCalc}$ or TMEM$_{MenaINV}$ predicts response to cytotoxic chemo, RTK and TK inhibitors and combination therapies involving both. Comparison of TMEM$_{MenaINV}$ in the presence of drug to TMEM$_{MenaINV}$ in the absence of drug provides companion diagnostic information for response to cytotoxic chemo, RTK inhibitors and combination therapies involving both.

REFERENCES

Agarwal S, Gertler F B, Balsamo M, Condeelis J S, Camp R L, Xue X, Lin J, Rohan T E, Rimm D L (2012) Quantitative assessment of invasive mena isoforms (Menacalc) as an independent prognostic marker in breast cancer. Breast Cancer Research. 14(5):R124.

Condeelis J, Singer R H, Segall J E (2005) The great escape: when cancer cells hijack the genes for chemotaxis and motility. Annu Rev Cell Dev Biol. 21: 695-718.

Eddy, R J, Weidmann, M and Condeelis, J. S. (2017) Tumor cell invadopodia: Invasive protrusions that orchestrate metastasis. Trends in Cell Biology (8):595-607. Epub 2017 Apr. 12.

Forse C L, Agarwal S, Pinnaduwage D, Gertler F, Condeelis J S, Lin J, Xue X, Johung K, Mulligan A M, Rohan T E, Bull S B, Andrulis I L (2015) Menacalc, a quantitative method of metastasis assessment, as a prognostic marker for axillary node-negative breast cancer. BMC Cancer. 15:483.

Harney A S, Karagiannis G S, Pignatelli J, Smith B D, Kadioglu E, Wise S C, Hood M M, Kaufman M D, Leary C B, Lu W P, Al-Ani G, Chen X, Entenberg D, Oktay M H, Wang Y, Chun L, De Palma M, Jones J G, Flynn D L, Condeelis J S. (2017). The selective Tie2 inhibitor rebastinib blocks recruitment and function of Tie2$^{Hi}$ macrophages in breast cancer and pancreatic neuroendocrine tumors. Mol Cancer Ther. 16(11) 2486-2501. EPub Aug. 24, 2017. PMID: 28838996.

Karagiannis, G. S., Goswami, S., Jones, J. G., Oktay, M. H., and Condeelis, J. S (2016) Signatures of breast cancer metastasis at a glance. Journal of Cell Science. 129, 1751-1758. PMID: 27084578/PMCID: PMC48993654.

Karagiannis G. S., J. M. Pastoriza, Y. Wang, A. S. Harney, D. Entenberg, J. Pignatelli, V. P. Sharma, E. A. Xue, E. Cheng, T. M. D'Alfonso, J. G. Jones, J. Anampa, T. E. Rohan, J. A. Sparano, J. S. Condeelis, M. H. Oktay (2017) Neoadjuvant chemotherapy induces breast cancer metastasis through a TMEM-mediated mechanism, Science Translational Medicine 9(397).

Leung E, Xue A, Wang Y, Rougerie P, Sharma V, Eddy, R., Cox, D. and John Condeelis. (2016) Blood vessel endothelium—directed tumor cell streaming in breast tumors requires the HGF/C-Met signaling pathway. Oncogene. 1-13. PMID: 27893712.

Patsialou A, Wang Y, Lin J, Whitney K, Goswami S, Kenny P, Condeelis J, (2012) Selective gene-expression profiling of migratory tumor cells in vivo predicts clinical outcome in breast cancer patients. Breast Cancer Res. 14(5):R139.

Pignatelli J, Bravo-Cordero J J, Roh-Johnson M, Gandhi S J, Wang Y, Chen X, Eddy R J, Xue A, Singer R H, Hodgson L, Oktay M H, Condeelis J S (2016) Macrophage-dependent tumor cell transendothelial migration is mediated by Notch1/MenaINV-initiated invadopodium formation. Scientific Reports. 6:37874.

Pignatelli J, Goswami S, Jones J G, Rohan T E, Pieri E, Chen X, Adler E, Cox D, Maleki S, Bresnick A, Gertler F B, Condeelis J S, Oktay M R (2014) Invasive breast carcinoma cells from patients exhibit MenaINV- and macrophage-dependent transendothelial migration. Science Signaling. 7(353):ra112.

Rohan T E, Xue X, Lin H M, D'Alfonso T M, Ginter P S, Oktay M H, Robinson B D, Ginsberg M, Gertler F B, Glass A G, Sparano J A, Condeelis J S, Jones J G (2014) Tumor microenvironment of metastasis and risk of distant metastasis of breast cancer. Journal of the National Cancer Institute. 106(8).

Roussos E T, Balsamo M, Alford S K, Wyckoff J B, Gligorijevic B, Wang Y, Pozzuto M, Stobezki R, Goswami S, Segall J E, Lauffenburger D A, Bresnick A R, Gertler F B, Condeelis J S (2011a) Mena invasive (MenaINV) promotes multicellular streaming motility and transendothelial migration in a mouse model of breast cancer. Journal of Cell Science. 124 (Pt 13):2120-31.

Roussos E T, Goswami S, Balsamo M, Wang Y, Stobezki R, Adler E, Robinson B D, Jones J G, Gertler F B, Condeelis J S, Oktay M H (2011b) Mena invasive (Mena(INV)) and Mena11a isoforms play distinct roles in breast cancer cell cohesion and association with TMEM. Clinical & Experimental Metastasis. 28(6):515-27.

Weidmann M D, Surve C R, Eddy R J, Chen X, Gertler F B, Sharma V P, Condeelis J S (2016) MenaINV dysregulates cortactin phosphorylation to promote invadopodium maturation. Scientific Reports 6:36142.

U.S. Pat. No. 8,603,738 B2, issued Dec. 10, 2013, Condeelis et al. Metastasis specific splice variants of Mena and uses thereof in diagnosis, prognosis and treatment of tumors.

U.S. Pat. No. 8,642,277 B2, issued Feb. 4, 2014, Condeelis et al. Tumor microenvironment of metastasis (TMEM) and uses thereof in diagnosis, prognosis and treatment of tumors.

PCT International Publication No. WO 2016/191401, published Dec. 1, 2016, Albert Einstein College of Medicine, INC., Condeelis and Harney, TMEM active test and uses thereof in diagnosis, prognosis and treatment of tumors.

What is claimed is:

1. A method for detecting a hematogenous metastatic cancer in a subject or detecting tumor cells from the subject undergoing hematogenous metastasis, the method comprising:
   i) obtaining from a subject a cancer tissue sample stained for a presence of macrophages, endothelial cells, and one or more of pan-Mena, MenaINV, and Mena11a;
   ii) identifying regions of a tumor microenvironment of metastasis (TMEM) within the tissue sample, wherein the TMEM is defined by:
      (a) juxtaposition of a macrophage, an endothelial cell, and an invasive tumor cell, wherein an invasive tumor cell is identified by expression of high pan-Mena, MenaCalc, and/or MenaINV; or
      (b) a Tie2Hi/VEGFHi macrophage in direct contact with a blood vessel with decreased VE-Cadherin and/or ZO-1 endothelial staining;
   iii) determining if the sample has a High or Low TMEM Score, where a TMEM Score is the High TMEM Score if a TMEM count in a number (N) of TMEM fields of view is above a predetermined threshold ($TMEM_{cut}$), and the TMEM Score is the Low TMEM Score if the TMEM count in the number (N) of TMEM fields of view is equal to or below the $TMEM_{cut}$ and;
   iv) performing within a specified distance from the TMEM, in a highest ranked TMEM fields of view, a determination of one or both of:
      a) levels of MenaINV, or
      b) levels of pan-Mena and Mena11a, and for b), calculating MenaCalc, where MenaCalc equals levels of pan-Mena minus levels of Mena11a;

v) determining if:
   a) the sample has a High or Low MenaINV Score, where the MenaINV Score is the High MenaINV Score when the MenaINV score in the highest ranked TMEM fields of view is above a predetermined threshold (MenaINV$_{cut}$), and where the MenaINV Score is the Low MenaINV Score when the MenaINV score in the highest ranked TMEM fields of view is equal to or below the MenaINV$_{cut}$, and/or
   b) the sample has a High or Low MenaCalc Score, where the MenaCalc Score is the High MenaCalc Score when the MenaCalc score in the highest ranked TMEM fields of view is above a predetermined threshold (MenaCalc$_{cut}$), and where the MenaCalc Score is the Low MenaCalc Score when the MenaCalc score in the highest ranked TMEM fields of view is equal to or below the MenaCalc$_{cut}$; and
vi) detecting a hematogenous metastatic cancer in the subject or detecting tumor cells from the subject undergoing hematogenous metastasis if the sample has:
   a) both the High TMEM Score and the High MenaINV Score, and/or
   b) both the High TMEM Score and the High MenaCalc Score;
wherein a presence of the Low TMEM Score and/or the Low MenaINV Score, or a presence of the Low TMEM Score and/or the Low MenaCalc Score indicates that the subject does not have the hematogenous metastatic cancer or does not have tumor cells undergoing hematogenous metastasis.

2. The method of claim 1, wherein i) the TMEM score and ii) the MenaINV Score or MenaCalc Score are obtained from serial sections of the sample which are aligned or co-registered.

3. The method of claim 1, wherein i) the TMEM score and ii) the MenaINV Score or MenaCalc Score are obtained from the same section of the sample.

4. The method of claim 3, comprising staining the TMEM, the MenaINV, the pan-Mena, or the Mena11a by multiplex staining.

5. The method of claim 1, wherein the cancer tissue sample is a breast, pancreas, prostate, colon, brain, liver, lung, head, or neck tumor sample.

6. The method of claim 1, comprising detecting an endothelial cell of the TMEM by detecting CD31 in the sample.

7. The method of claim 1, comprising detecting a macrophage of the TMEM by detecting CD68 in the sample.

8. The method of claim 1, comprising detecting the endothelial cells, the macrophages, and/or the invasive tumor cells using antibodies, monoclonal antibodies, antibody fragments, peptides, aptamers, and/or cDNA probes that are specific for their target.

9. The method of claim 1, wherein the specified distance from TMEM regions is within a 1 mm radius of the TMEM regions.

10. The method of claim 1, wherein the specified distance from TMEM regions is not less than a 500 µm radius of the TMEM regions.

11. The method of claim 1, comprising determining a TMEM$_{MenaINV}$ Score by:

$$TMEM_{MenaINV} = \left(\sum_i^M TMEM_i > TMEM_{cut}\right) \wedge \left(\sum_j^N \frac{\left(\frac{\iint MenaINV\, ds_j}{\iint ds_j}\right)}{N} > MenaINV_{cut}\right).$$

12. The method of claim 1, comprising determining a TMEM$_{MenaCalc}$ Score by:

$$TMEM_{MenaCalc} = \left(\sum_i^M TMEM_i > TMEM_{cut}\right) \wedge \left(\sum_j^N \frac{\left(\frac{\iint MenaCalc\, ds_j}{\iint ds_j}\right)}{N} > MenaCalc_{cut}\right).$$

13. The method of claim 1, comprising determining a TMEM$_{MenaCalc}$ Score by:

$$TMEM_{MenaCalc} = \frac{A\left(\sum_i^M TMEM_i\right) + B\left(\sum_j^N \frac{\left(\frac{\iint MenaCalc\, ds_j}{\iint ds_j}\right)}{N}\right)}{A + B}.$$

14. The method of claim 1, comprising determining a TMEM$_{MenaINV}$ Score by:

$$TMEM_{MenaINV} = \frac{A\left(\sum_i^M TMEM_i\right) + B\left(\sum_j^N \frac{\left(\frac{\iint MenaINV\, ds_j}{\iint ds_j}\right)}{N}\right)}{A + B}.$$

15. A method of treating a hematogenous metastatic cancer in a subject in need thereof, comprising:
   a) determining if a subject has a hematogenous metastatic cancer or if the subject has tumor cells undergoing hematogenous metastasis according to the method of claim 1; and
   b) administering an anti-cancer therapy to the subject identified as having the hematogenous metastatic cancer or having the tumor cells undergoing hematogenous metastasis.

16. The method of claim 15, wherein the anti-cancer therapy comprises one or more of a cytotoxic chemotherapy drug, a receptor tyrosine kinase inhibitor, a tyrosine kinase inhibitor, an EGFR, HGFR, IGFR, CSFIR, Tie2 or VEGFR inhibitor, an Src, Abl or Arg inhibitor, rebastinib (4-[4-[(5-tert-butyl-2-quinolin-6-ylpyrazol-3-yl) carbamoylamino]-3-fluorophenoxy]-N-methylpyridine-2-carboxamide), an anti-tubulin chemotherapy, a taxane, a non-taxane microtubule inhibitor, a topoisomerase inhibitor, an intercalating agent, a DNA cross-linking agent, an alkylating agent, radiation and surgery, or combinations thereof.

17. The method of claim 1, comprising: scoring the TMEM in a tumor tissue, and scoring the MenaCalc and/or the MenaINV in a blood sample from the same subject to determine the Mena expression status of tumor cell intravasation.

18. The method of claim 17, wherein one or more of an antibody, an antibody fragment, a peptide, an aptamer, and a cDNA probe are used to detect and score MenaCalc and/or MenaINV levels.

19. The method of claim 17, wherein MenaCalc and/or MenaINV levels are determined using a DDCt PCR with cDNA primers specific to a Mena slice variant, and wherein all MENA Ct values in the tumor tissue are normalized to glyceraldehyde 3-phosphate dehydrogenase (GAPDH).

20. The method of claim 17, comprising determining a $TMEM_{MenaCalc}$ score by:

$$TMEM_{MenaCalc} = \frac{A\left(\sum_i^N TMEM_i\right) + B(DDCtMenaCalc)/DDCtGAPDH}{A+B}.$$

21. The method of claim 1, comprising assigning the TMEM Score, the MenaINV Score, and/or the MenaCalc Score a quantitative value.

22. A method for detecting a hematogenous metastatic cancer in a subject or detecting tumor cells from the subject-undergoing hematogenous metastasis, the method comprising:
Obtaining a sample of a cancer from a subject;
staining the sample to identify a presence of a tumor microenvironment of metastasis (TMEM);
performing image analysis on the sample stained for the TMEM and quantifying a TMEM distribution in the sample;
determining if a number (N) of different regions of the TMEM distribution in the sample is (i) above a predetermined threshold of TMEM distribution ($TMEM_{cut}$) so as to obtain a High TMEM score or (ii) equal to or below the $TMEM_{cut}$ so as to obtain a Low TMEM score, wherein the Low TMEM score indicates that the subject does not have a hematogenous metastatic cancer or does not tumor cells undergoing hematogenous metastasis;
if a TMEM score is the High TMEM score, determining a spatial center for each of the number of different regions of the TMEM distribution in the sample that are above a predetermined threshold;
staining the sample for a presence of MenaINV or for a presence of pan-Mena and Mena11a;
performing image analysis on the sample stained for MenaINV or pan-Mena and Mena11a, and quantifying MenaINV or pan-Mena and Mena11a within a predetermined area centered on each of spatial centers (MenaINV or MenaCalc, respectively) of the N different regions of TMEM, wherein MenaCalc is defined by pan-Mena quantified minus Mena11a quantified;
normalizing the MenaINV or MenaCalc values for a size of the predetermined area;
determining if a total normalized MenaINV is (i) above a predetermined value ($MenaINV_{cut}$) so as to obtain a High MenaINV score or (ii) equal to or below the $MenaINV_{cut}$ so as to obtain a Low MenaINV score; and/or determining if the total normalized MenaCalc is (i) above a predetermined value ($MenaCalc_{cut}$) so as to obtain a High MenaCalc score or (ii) equal to or below the MenaCalc cut so as to obtain a Low MenaCalc score; and
detecting a hematogenous metastatic cancer in the subject or detecting tumor cells from the subject undergoing hematogenous metastasis if the sample has:
a) both the High TMEM Score and the High MenaINV Score, and/or
b) both the High TMEM Score and the High MenaCalc Score;
wherein a presence of the Low TMEM Score and/or the Low MenaINV Score, or a presence of the Low TMEM Score and/or the Low MenaCalc Score indicates that the subject does not have a hematogenous metastatic cancer or does not have tumor cells undergoing hematogenous metastasis.

23. The method of claim 22, wherein the predetermined area is within a radius of from 500 μm to 1 mm of the spatial center of regions of TMEM distribution in the sample which are above the predetermined threshold.

24. The method of claim 22, wherein staining the sample to identify the presence of the TMEM and staining the sample for the presence of the MenaINV or for the presence of the pan-Mena and the Mena11a are performed prior to determining the spatial center for each of the number of different regions of the TMEM distribution in the sample that are above the predetermined threshold.

25. The method of claim 24, comprising: (i) aligning an image of the sample stained for the TMEM and an image of the sample stained for the pan-Mena and the Mena11a to a single cell level prior to performing the image analysis on the sample stained for the TMEM, and (ii) quantifying the TMEM distribution in the sample or prior to determining the number (N) of different regions of the TMEM distribution in the sample which are above the predetermined threshold of TMEM distribution ($TMEM_{cut}$).

* * * * *